(12) United States Patent
Hernandez et al.

(10) Patent No.: US 9,393,375 B2
(45) Date of Patent: Jul. 19, 2016

(54) NASAL VENTILATION INTERFACE

(75) Inventors: Shara Hernandez, Davie, FL (US); Louis Javier Collazo, Pompano Beach, FL (US)

(73) Assignee: Mergenet Solutions, Coconut Creek, FL (US)

( * ) Notice: Subject to any disclaimer, the term of this patent is extended or adjusted under 35 U.S.C. 154(b) by 1002 days.

(21) Appl. No.: 12/349,539

(22) Filed: Jan. 7, 2009

(65) Prior Publication Data

US 2009/0173349 A1 Jul. 9, 2009

Related U.S. Application Data

(60) Provisional application No. 61/006,336, filed on Jan. 7, 2008.

(51) Int. Cl.
*A61M 16/06* (2006.01)
*A61M 16/08* (2006.01)

(52) U.S. Cl.
CPC ............ *A61M 16/06* (2013.01); *A61M 16/0616* (2014.02); *A61M 16/0633* (2014.02); *A61M 16/0666* (2013.01); *A61M 16/0683* (2013.01); *A61M 16/0816* (2013.01); *A61M 16/0833* (2014.02); *A61M 16/0875* (2013.01); *A61M 2210/0618* (2013.01)

(58) Field of Classification Search
CPC ............ A61M 16/06; A61M 16/0666; A61M 16/0672; A61M 16/0683; A61M 16/0618; A61M 2210/0618; A61M 25/005; A61M 25/0012; A61M 25/0266; A61M 2025/0035; A61M 25/0028

USPC ............ 128/206.11, 206.21, 207.13, 207.18; 604/524; 138/153, 172
See application file for complete search history.

(56) References Cited

U.S. PATENT DOCUMENTS

| | | | | | |
|---|---|---|---|---|---|
| 4,278,082 | A | * | 7/1981 | Blackmer | 128/207.18 |
| 4,406,283 | A | * | 9/1983 | Bir | 128/207.18 |
| 4,737,153 | A | * | 4/1988 | Shimamura et al. | 604/526 |
| 5,176,660 | A | * | 1/1993 | Truckai | 604/527 |
| 5,456,674 | A | * | 10/1995 | Bos et al. | 604/526 |
| 5,509,408 | A | * | 4/1996 | Kurtis | 128/207.14 |
| 5,546,936 | A | * | 8/1996 | Virag et al. | 128/207.14 |
| 5,643,174 | A | * | 7/1997 | Yamamoto et al. | 600/114 |
| 5,827,242 | A | * | 10/1998 | Follmer et al. | 604/526 |
| 5,863,366 | A | * | 1/1999 | Snow | 156/143 |
| 6,148,818 | A | * | 11/2000 | Pagan | 128/207.15 |
| 6,273,876 | B1 | * | 8/2001 | Klima et al. | 604/264 |
| 6,595,215 | B2 | * | 7/2003 | Wood | 128/207.18 |

(Continued)

OTHER PUBLICATIONS

International Search Report dated Jul. 31, 2009 to corresponding international patent application No. PCT/US2009/030258, 3 pages.

(Continued)

*Primary Examiner* — Justine Yu
*Assistant Examiner* — Douglas Sul
(74) *Attorney, Agent, or Firm* — Maier & Maier, PLLC

(57) ABSTRACT

A ventilation interface may include the following elements: a cushion, shell, forehead support, supply tubes, an adapter or Y-connector and a nasal cannula, which may also include nasal inserts, and connectors. Each of the elements of the ventilation interface may also include ribs of wire, stiffener or other bendable material having a greater rigidity than the material composing the main body of each element. These bendable portions may be capable of retaining multiple desired bent shapes in multiple desired directions.

17 Claims, 16 Drawing Sheets

(56) References Cited

U.S. PATENT DOCUMENTS

| | | | |
|---|---|---|---|
| 6,772,761 B1 * | 8/2004 | Rucker, Jr. | 128/207.14 |
| 6,776,162 B2 | 8/2004 | Wood | |
| 6,807,967 B2 | 10/2004 | Wood | |
| 6,994,089 B2 | 2/2006 | Wood | |
| 6,997,187 B2 | 2/2006 | Wood et al. | |
| 7,000,613 B2 | 2/2006 | Wood et al. | |
| 7,018,372 B2 * | 3/2006 | Casey et al. | 604/524 |
| 7,047,974 B2 | 5/2006 | Strickland et al. | |
| 7,059,328 B2 | 6/2006 | Wood | |
| 7,178,524 B2 * | 2/2007 | Noble | A61M 16/01 128/206.11 |
| 7,188,624 B2 | 3/2007 | Wood | |
| 7,191,781 B2 | 3/2007 | Wood | |
| D550,836 S | 9/2007 | Chandran et al. | |
| 7,406,966 B2 * | 8/2008 | Wondka | 128/207.18 |
| 7,559,327 B2 | 7/2009 | Hernandez | |
| 7,814,911 B2 * | 10/2010 | Bordewick et al. | 128/207.13 |
| 8,042,539 B2 | 10/2011 | Chandran et al. | |
| 8,136,527 B2 * | 3/2012 | Wondka | 128/207.18 |
| 2002/0059935 A1 * | 5/2002 | Wood | 128/207.18 |
| 2004/0000314 A1 * | 1/2004 | Angel | 128/207.14 |
| 2005/0066976 A1 * | 3/2005 | Wondka | 128/207.18 |
| 2006/0081252 A1 | 4/2006 | Wood | |
| 2006/0107958 A1 * | 5/2006 | Sleeper | 128/206.11 |
| 2006/0174887 A1 | 8/2006 | Chandran et al. | |
| 2006/0180151 A1 | 8/2006 | Rinaldi | |
| 2007/0010786 A1 * | 1/2007 | Casey et al. | 604/95.04 |
| 2007/0221226 A1 | 9/2007 | Hansen et al. | |
| 2007/0272249 A1 | 11/2007 | Chandran et al. | |

OTHER PUBLICATIONS

U.S. Appl. No. 60/634,802, filed Dec. 10, 2004, Sanjay Chandran.

\* cited by examiner

NASAL VENTILATION INTERFACE

RELATED APPLICATIONS

This application claims priority, under 35 U.S.C. §119(e), to U.S. Provisional Patent Application Ser. No. 61/006,336, filed Jan. 7, 2008, the disclosure of which is incorporated by reference herein in its entirety.

BACKGROUND

Nasal ventilators generally consist of tubes and other means for delivering gases adapted for use with the nasal or oral passages of a patient. Typically, a nasal ventilation system comprises a gas source and a mechanical ventilator such as a continuous positive airway pressure system (CPAP), bi-level positive airway pressure system (BIPAP), or intermittent (non-continuous) positive pressure (IPPB). The gas is often room air or oxygen-enriched air, but can be a mixture of other gases.

The gas is transported by a thin flexible tube made of an inert material. The tube terminates in an opening which can be inserted into the patient's nostrils. Typically, a pair of smaller nasal insert tubes protrudes from the tube or the tube splits at a Y-junction into two smaller tubes, each smaller nasal insert tube carrying gas to one nostril, thereby increasing the fraction of inspired oxygen.

Moreover, conventional nasal ventilation systems use head gear and/or straps to bind the mask in place, but in order to minimize the leakage of the air the straps must be sufficiently tight. The mask, headgear, and/or straps thereby exert pressure on the patient's face and/or head.

SUMMARY

An exemplary embodiment discloses a ventilation interface that may include the following elements: supply tubes, an adapter or Y-connector and a nasal cannula, which may also include nasal inserts, and connectors. Each of the elements of the ventilation interface may also include ribs of wire, stiffener or other bendable material having a greater rigidity than the material composing the main body of each element. These bendable portions may be capable of retaining multiple desired bent shapes in multiple desired directions.

Another exemplary embodiment discloses a ventilation interface that may include the following elements: a cushion, shell and forehead support. Each of the elements of the ventilation interface may also include ribs of wire, stiffener or other bendable material having a greater rigidity than the material composing the main body of each element. These bendable portions may be capable of retaining multiple desired bent shapes in multiple desired directions.

BRIEF DESCRIPTION OF THE DRAWINGS

Advantages of embodiments of the ventilation interface will be apparent from the following detailed description of the exemplary embodiments thereof, which description should be considered in conjunction with the accompanying drawings in which like numerals indicate like elements, in which:

FIG. 10b is an exemplary section view along the lines 10B-10B of FIG. 10a.

FIG. 11b is an exemplary section view along the lines 11B-11B of FIG. 11a.

FIG. 12b is an exemplary section view along the lines 12B-12B of FIG. 12a.

FIG. 13b is an exemplary section view along the lines 13B-13B of FIG. 13a.

FIG. 14b is an exemplary section view along the lines 14B-14B of FIG. 14a.

Similar reference characters denote corresponding features consistently throughout the attached drawings.

DETAILED DESCRIPTION

Aspects of the disclosed embodiments are disclosed in the following description and related drawings directed to specific embodiments of the invention. Alternate embodiments may be devised without departing from the spirit or the scope of the ventilation interface. Additionally, well-known elements of exemplary embodiments of the ventilation will not be described in detail or will be omitted so as not to obscure the relevant details of the invention. Further, to facilitate an understanding of the description, discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the ventilation interface" does not require that all embodiments of the ventilation interface include the discussed feature, advantage or mode of operation.

Other examples of the below-described invention may be used or adapted to be used with the following U.S. Pat. Nos. 6,595,215, 6,776,162, 6,807,967, 6,994,089, 6,997,187, 7,000,613, 7,047,974, 7,059,328, 7,188,624, and 7,191,781 and pending US patent applications and publications 20060124131, 29/245,378, 60/634,802, Ser. Nos. 11/139, 496, 11/298,679, 11/372,025, 11/430,902, 11/175,683 all of which are hereby incorporated by reference in their entirety.

Figure 1:
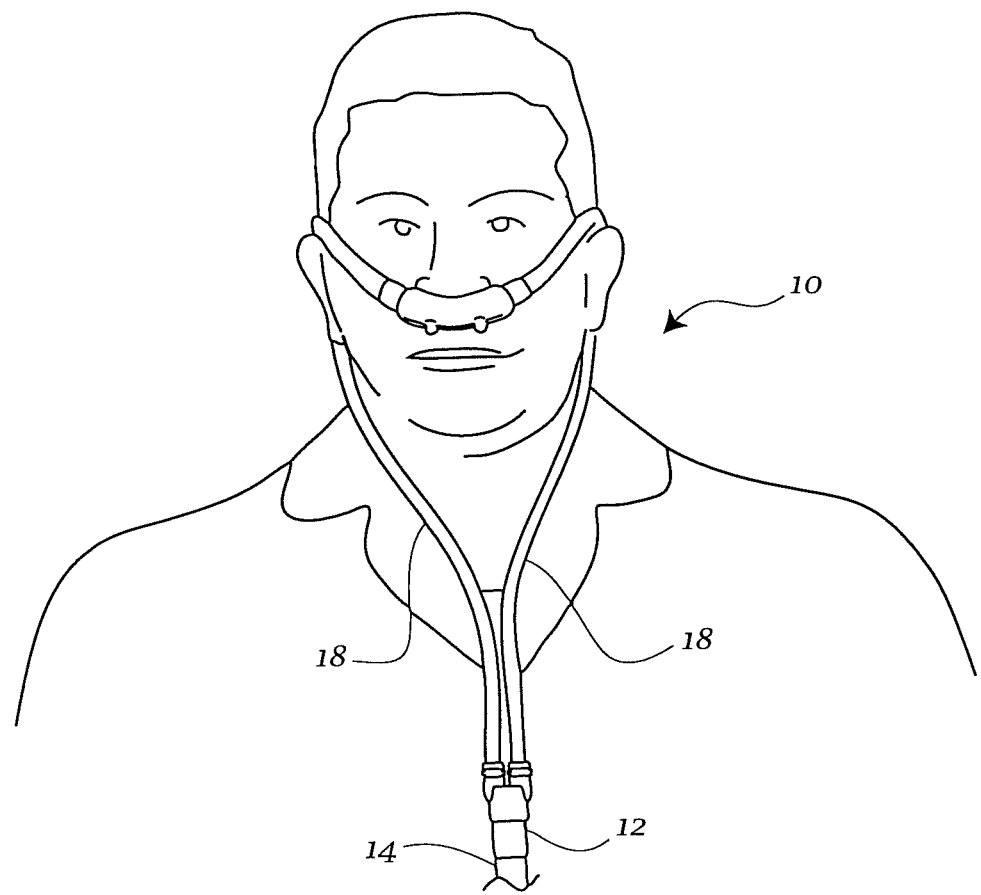
FIG. 1 is an exemplary front environmental view of an exemplary ventilation interface.
Figure 2:
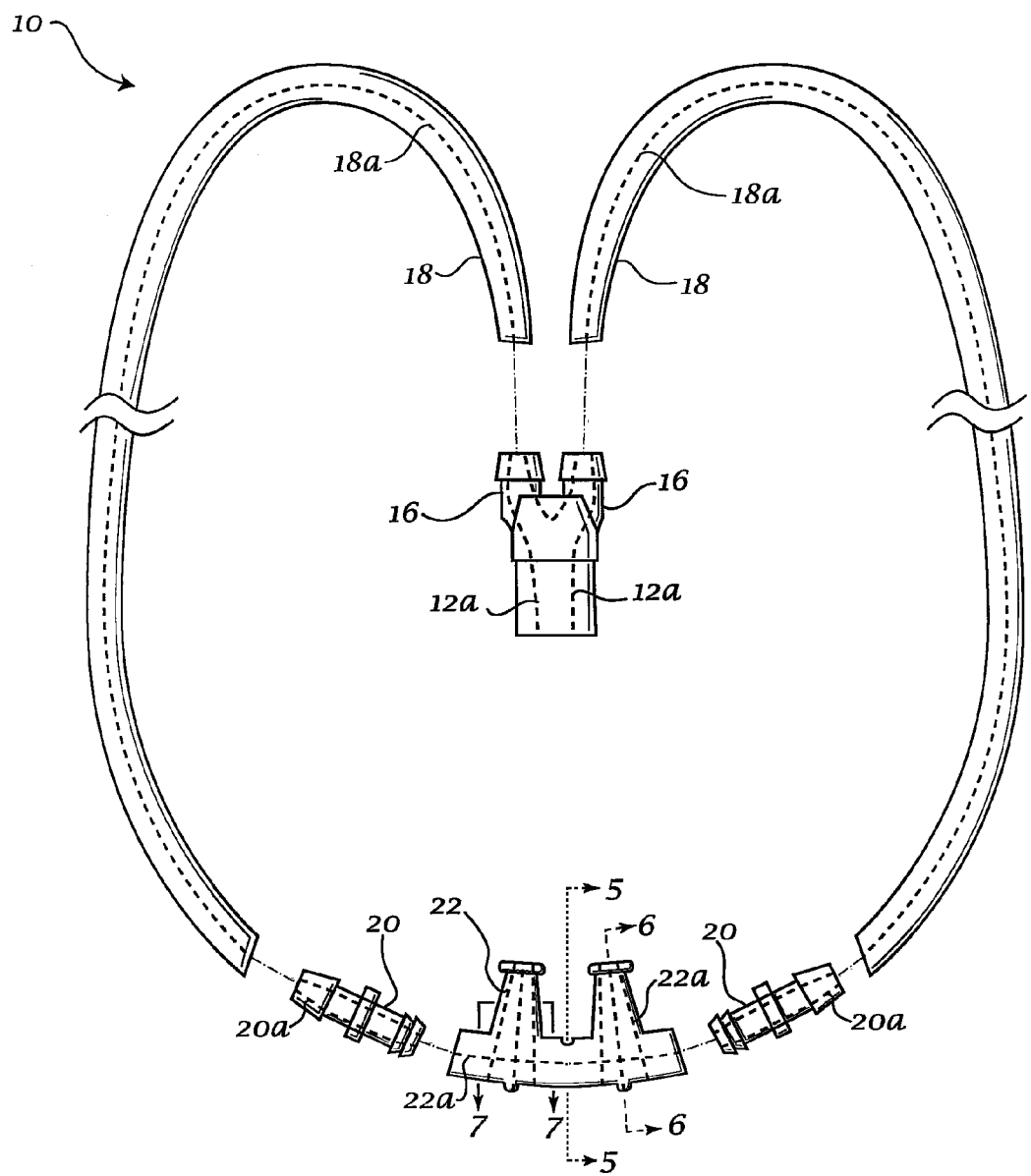
FIG. 2 is an exemplary exploded elevated view of an exemplary ventilation interface.
Figure 3:
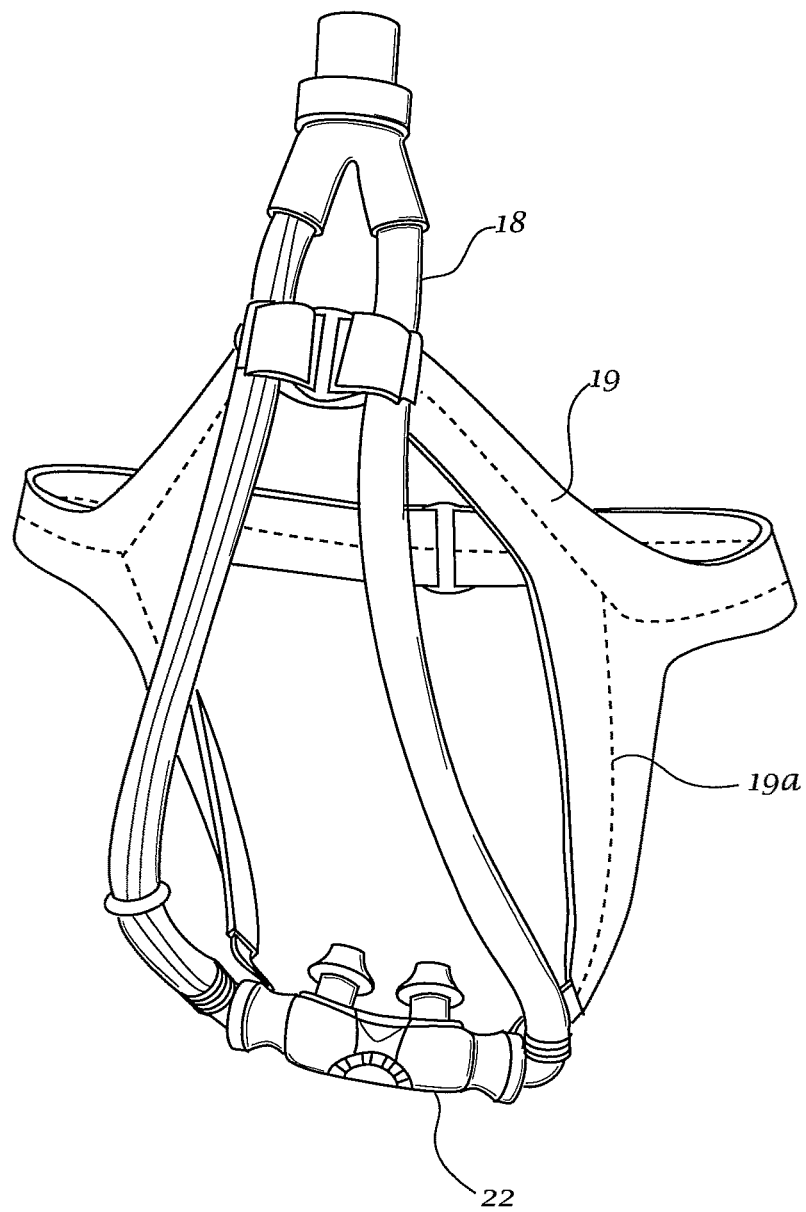
FIG. 3 is an exemplary perspective view of an exemplary ventilation interface with an exemplary head gear.

An exemplary embodiment of a ventilation interface 10 for sleep apnea therapy is depicted generally in the FIGS. 1-7 and 9a-9d. The ventilation interface 10 may provide an interface for connecting a ventilation device which provides positive airway pressure (either continuous, bilevel, or intermittent) with the patient's airways. As shown in FIGS. 1-3, the ventilation interface 10 may include a conventional adapter or Y-connector 12 having a first end adapted to receive a supply hose 14 from a mechanical ventilator (not shown) and a second end having a pair of ports 16 with barbed connectors for attachment to two supply tubes 18. Supply tubes 18 may be flexchem tubing, made of polyvinyl chloride or other desired conventional gas supply tubing.

As seen in FIG. 2, Y-connector 12 may also include Y-connector ribs 12a made of memory wire, stiffener or other desired bendable material that may have a greater rigidity than the material composing the main body of the Y-connector 12. These Y-connector ribs 12a may be capable of being contorted into and retaining multiple desired bent shapes. The Y-connector ribs 12a may be formed, for example, vertically along the length of the Y-connector 12, as seen in FIG. 2, or circumferentially throughout the length of the Y-connector 12 or in any other desired configuration. The number of Y-connector ribs 12a used may vary according to preference, ranging from at least one Y-connector rib 12a, to as many as desired. The Y-connector ribs 12a may also be of any desired length or thickness. Increasing the number and size of Y-connector ribs 12a may increase the rigidity of the Y-connector 12 incrementally.

The Y-connector ribs 12a may be made of plastic, metal or any other material that may be capable of adding rigidity and shape retention. The Y-connector ribs 12a may be manufactured within the walls of the Y-connector 12 or lie on the outer or inner surface of the Y-connector 12. The Y-connector ribs 12a may be secured to the Y-connector 12 by, for example, insert molding, gluing or by any other desired attachment mechanism. Y-connector ribs 12a may also have a variety of different cross sectional shapes, for example, circular, rectangular, square or any other desired shape. The cross sectional shape may also change through different sections over the length of the Y-connector ribs 12a. Additionally, Y-connector ribs 12a may have a continuous length or have non-continuous sections. The Y-connector ribs 12a may provide a user with the ability to manipulate the structure of the Y-connector 12 whereby improving comfort and convenience during use, as well as, improved seal ability and air flow.

As seen in FIG. 2, supply tube 18 may also include supply tube ribs 18a made of memory wire, stiffener or other desired bendable material that may have a greater rigidity than the material composing the main body of the supply tube 18. These supply tube ribs 18a may be capable of being contorted into and retaining multiple desired bent shapes. The supply tube ribs 18a may be formed, for example, vertically along the length of the supply tube 18, as seen in FIG. 2, or circumferentially throughout the length of the supply tube or in any other desired configuration. The number of supply tube ribs 18a used may vary according to preference, ranging from at least one supply tube rib, to as many as desired. The supply tube ribs 18a may also be of any desired length or thickness. Increasing the number and size of supply tube ribs 18a may increase the rigidity of the supply tube 18 incrementally.

The supply tube ribs 18a may be made of plastic, metal or any other material that may be capable of adding rigidity and shape retention. The supply tube ribs 18a may be manufactured within the walls of the supply tube 18 or lie on the outer or inner surface of the supply tube 18. The supply tube ribs 18a may be secured to the supply tube 18 by, for example, insert molding, gluing or by any other desired attachment mechanism. Supply tube ribs 18a may also have a variety of different cross sectional shapes, for example, circular, rectangular, square or any other desired shape. The cross sectional shape may also change through different sections over the length of the supply tube ribs 18a. Additionally, supply tube ribs 18a may have a continuous length or have non-continuous sections. The supply tube ribs 18a may provide a user with the ability to manipulate the structure of the supply tube 18 whereby improving comfort and convenience during use, as well as, improved sealability and air flow.

In the embodiment shown in FIGS. 1 and 2, the ends of the supply tubes 18 distal from the Y-connector 12 may be attached to opposite ends of a nasal cannula body 22 by barbed connectors 20. Barbed connectors 20 may have an inside diameter substantially equal to the inside diameter of supply tubes 18 in order to prevent any constriction or narrowing of the air passage which may cause increased velocity in air flow.

As seen in FIG. 2, barbed connectors 20 may also include barbed connector ribs 20a made of memory wire, stiffener or other desired bendable material that may have a greater rigidity than the material composing the main body of the barbed connectors 20. These barbed connector ribs 20a may be capable of being contorted into and retaining multiple desired bent shapes. The barbed connector ribs 20a may be formed, for example, vertically along the length of the barbed connectors 20, as seen in FIG. 2, or circumferentially throughout the length of the barbed connectors 20 or in any other desired configuration. The number of barbed connector ribs 20a used may vary according to preference, ranging from at least one barbed connector rib 20a, to as many as desired. The barbed connector ribs 20a may also be of any desired length or thickness. Increasing the number and size of barbed connector ribs 20a may increase the rigidity of the barbed connectors 20 incrementally.

The barbed connector ribs 20a may be made of plastic, metal or any other material that may be capable of adding rigidity and shape retention. The barbed connector ribs 20a may be manufactured within the walls of the barbed connectors 20 or lie on the outer or inner surface of the barbed connectors 20. The barbed connector ribs 20a may be secured to the barbed connectors 20 by, for example, insert molding, gluing or by any other desired attachment mechanism. Barbed connector ribs 20a may also have a variety of different cross sectional shapes, for example, circular, rectangular, square or any other desired shape. The cross sectional shape may also change through different sections over the length of the barbed connector ribs 20a. Additionally, barbed connector ribs 20a may have a continuous length or have non-continuous sections. The barbed connector ribs 20a may provide a user with the ability to manipulate the structure of the barbed connectors 20 whereby improving comfort and convenience during use, as well as, improved sealability and air flow.

In an exemplary embodiment, as shown in FIG. 3, a nasal cannula body 22 and supply tubes 18 may be attached to a headgear 19. Headgear 19 may be used to secure nasal cannula body 22 in working position with respect to a user. Headgear 19 may also include headgear ribs 19a made of memory wire, stiffener or other desired bendable material that may have a greater rigidity than the material composing the main body of the headgear 19. These headgear ribs 19a may be capable of being contorted into and retaining multiple desired bent shapes. The headgear ribs 19a may be formed, for example, vertically along the length of the headgear 19, as seen in FIG. 3. The number of headgear ribs 19a used may vary according to preference, ranging from at least one headgear rib 19a, to as many as desired. The headgear ribs 19a may also be of any desired length or thickness. Increasing the number and size of headgear ribs 19a may increase the rigidity of the headgear 19 incrementally.

The headgear ribs 19a may be made of plastic, metal or any other material that may be capable of adding rigidity and shape retention. The headgear ribs 19a may be manufactured within the walls of the headgear 19 or lie on the outer or inner surface of the headgear 19. The headgear ribs 19a may be secured to the headgear 19 by, for example, sewing, molding, gluing or by any other desired attachment mechanism. Headgear ribs 19a may also have a variety of different cross sectional shapes, for example, circular, rectangular, square or any other desired shape. The cross sectional shape may also change through different sections over the length of the headgear ribs 19a. Additionally, headgear ribs 19a may have a continuous length or have non-continuous sections. The headgear ribs 19a may provide a user with the ability to manipulate the structure of the headgear 19 in any desired direction or shape, whereby improving comfort and convenience during use, as well as, improve the sizing of the headgear 19 for different sized users.

Figure 4:
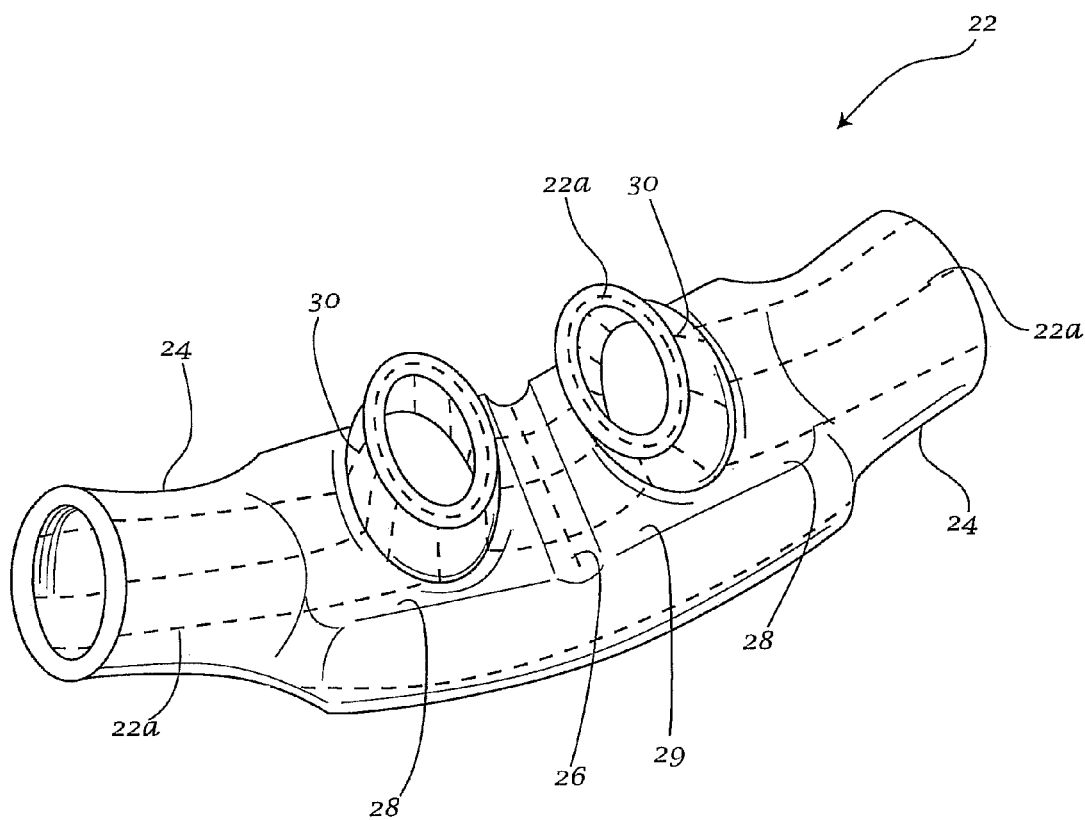
FIG. 4 is an exemplary perspective view of an exemplary ventilation interface embodied in an exemplary nasal cannula body.

In a further exemplary embodiment shown in FIGS. 4 and 9a-9d, nasal cannula body 22, may have a pair of nasal inserts 30 which may be inserted into the nares of a patient or user. Cannula body 22 may, for example, have an arcuate shape as shown in FIG. 4, or any other general shape or cross-sectional configuration. Cannula body 22 may also be formed of, for example, a hollow tube, mask or any other structure enabling the transfer of gas or fluid from a source to a specified destination, for example, the nares of a user.

In another exemplary embodiment cannula body 22 may be hollow and body 22 may, for example, have a sidewall 22b that may merge with a bottom wall 22c that may define an air chamber 22d (seen more clearly in FIG. 5) that may be utilized for the passage of air and other gases, and may have supply tubes 24 at opposite ends. In another exemplary embodiment, cannula body 22 may be in fluid communication with only a single supply tube 24 or as many different supply tubes 24 as desired. Supply tubes 24 may be connected to cannula body 22 at opposite ends, on the same end or at any other desired locations throughout the cannula body 22. Additionally, in a further exemplary embodiment cannula body 22 may be connected directly to a fluid supply or may be connected to a fluid supply by any other known conduit or gas supply structure.

In a further exemplary embodiment, a notch 26 may be defined transversely across a top wall 29 of cannula body 22, which may define a pair of mounting pads 28. A pair of nasal inserts 30 may be formed integrally with mounting pads 28. Additionally, nasal cannula body, for example, may be formed without notch 26, or alternatively, cannula body 22 may include any other structure or means for facilitating the bending or manipulation of cannula body 22. Nasal inserts 30 may also be, hollow and may, for example, form a flow path or conduit for the passage of gases between the patient's nasal air passages and the air chamber 22d.

Figure 5:
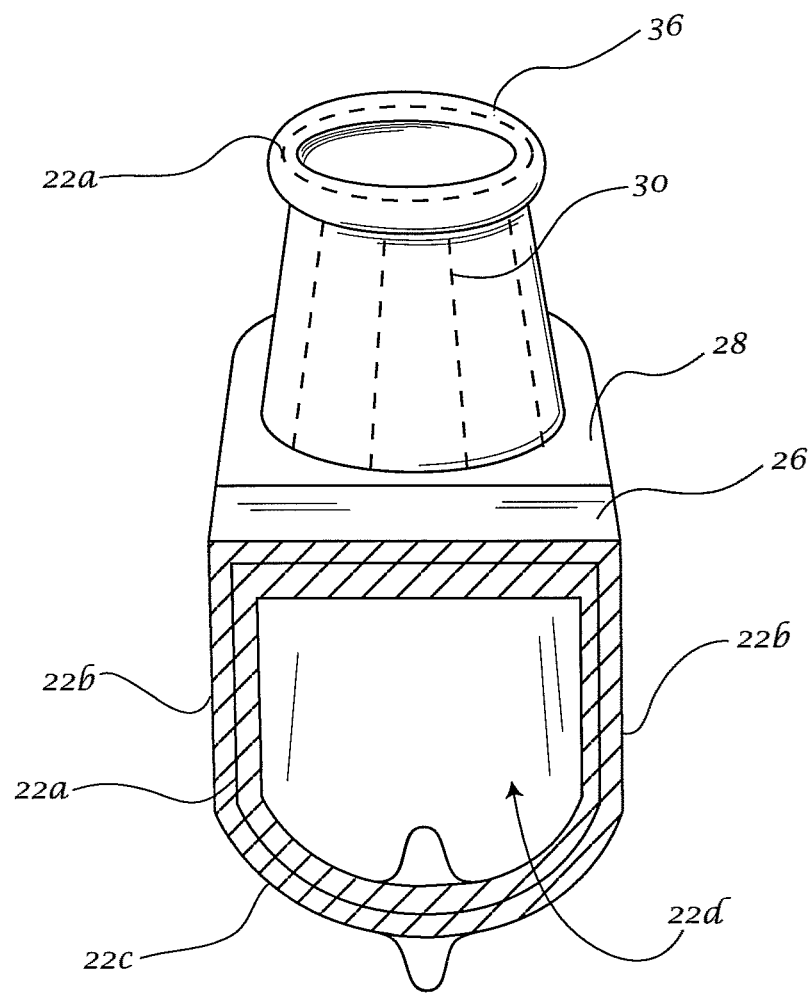
FIG. 5 is an exemplary section view along the lines 5-5 of FIG. 2.
Figure 6:
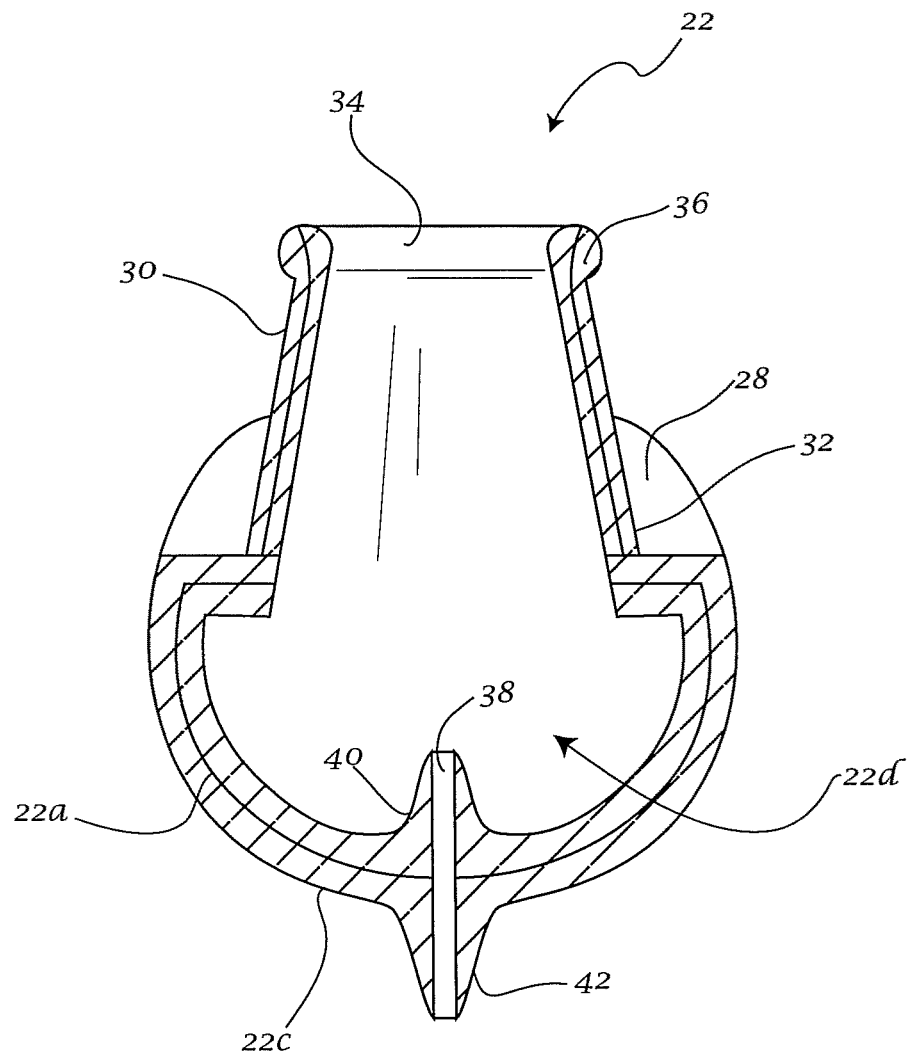
FIG. 6 is an exemplary section view along the lines 6-6 of FIG. 2.
Figure 7:
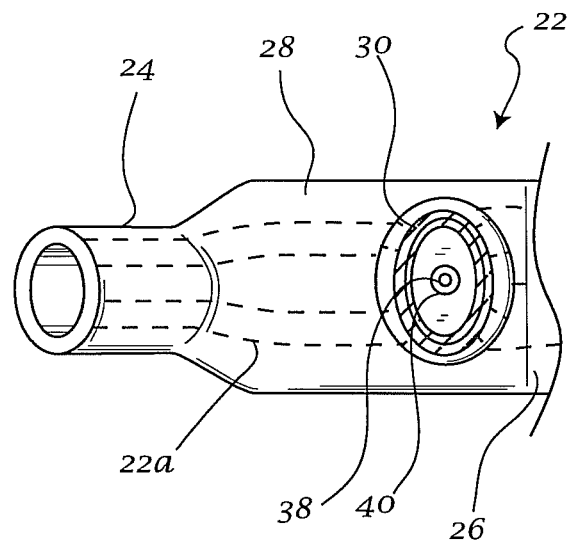
FIG. 7 is an exemplary section view along the lines 7-7 of FIG. 2.

In an additional exemplary embodiment, nasal inserts 30 are shown in greater detail in FIGS. 5, 6, and 7. The nasal inserts 30 may have any desired cross-sectional shape and may be positioned in any desired manner with respect to cannula body 22. Nasal inserts 30 may extend from a base 32 proximal the cannula body 22 to the open distal tip ends 34. The nasal inserts 30 may include a flange 36 about the distal tip ends 34 on the exterior surface of the inserts 30. Nasal inserts 30 may also be formed, for example, without a flange 36 or may incorporate any other additional structure that may aid in adding comfort or efficiency to the use of the nasal inserts.

In an exemplary embodiment, cannula body 22, including the nasal inserts 30, may be made from silicone elastomer or any other desired rigid or flexible material. In use, for example, the nasal inserts 30 may be inserted up the patient's nostrils until the flanges 36 lodge against the mucous membranes. As such, the nasal inserts 30 may be considered an invasive device. In alternative exemplary embodiments, nasal inserts 30 may not be inserted into the patients nostril's and may be positioned on the outside of the nostrils or the nasal inserts 30 may be positioned in any other desired location during use.

In another exemplary embodiment, notch 26, or any other desired structure enabling manipulation of cannula body 22, in cannula body 22 may lend additional flexibility to cannula body 22, so that nasal cannula body 22 can be adjusted for deviated septums, thick septums, and other anatomical variations in the configuration of the nostrils.

In a further exemplary embodiment, cannula body 22 may include a pair of bleeder ports 38 that may be disposed in bottom wall 22c which may be below nasal inserts 30. In other exemplary embodiments, cannula body 22 may not include a bleeder port 38, may include only one bleeder port 38 or include as many bleeder ports as desired. Additionally, for example, bleeder ports 38 may be located on any surface of cannula body 22 and in any desired configuration with respect to nasal ports 30. The bleeder ports 38 may be formed by an upper nipple 40 that may extend upward into the air chamber 22d, and a lower nipple 42 that may extend below the bottom wall 22c. Additionally, for example, the bleeder ports 38 may be formed without an upper nipple 40 and lower nipple 42 or may be formed by any other desired structure.

In another exemplary embodiment, as seen in FIGS. 4-7, cannula body 22 and nasal inserts 30 may also include cannula ribs 22*a* made of memory wire, stiffener or other desired bendable material that may have a greater rigidity than the material composing the main body of the cannula body 22 and nasal inserts 30. Cannula body 22 and nasal inserts 30 may be capable of being contorted into and retaining multiple desired bent shapes, as seen in FIGS. 9*a*-9*d*, for example, toward a users face, away from a users face or any other desired degree of bending or twisting. The cross-sectional shape of cannula body 22 and nasal inserts 30 may be altered throughout the entire structure or in only desired or predetermined locations, including, for example, the height, width or general shape in any desired direction. The cannula ribs 22*a* may be formed, for example, along the length of the cannula body 22 and nasal inserts 30, as seen in FIGS. 4-7, or circumferentially throughout the length of the cannula body 22 and nasal inserts 30 or in any other desired configuration. The number of cannula ribs 22*a* used may vary according to preference, ranging from at least one cannula rib 22*a*, to as many as desired. The cannula ribs 22*a* may also be of any desired length or thickness. Increasing the number and size of cannula ribs 22*a* may increase the rigidity of the cannula body 22 and nasal inserts 30 incrementally.

The cannula ribs 22*a* may be made of plastic, metal or any other material that may be capable of adding rigidity and shape retention. The cannula ribs 22*a* may be manufactured within the walls of the cannula body 22 and nasal inserts 30 or lie on the outer or inner surface of cannula body 22 and nasal inserts 30, as seen in FIGS. 10*a*-14*b*. The cannula ribs 22*a* may be secured to cannula body 22 and nasal inserts 30 by, for example, insert molding, gluing or by any other desired attachment mechanism. Cannula ribs 22*a* may also have a variety of different cross sectional shapes, for example, circular, rectangular, square or any other desired shape, as seen in FIGS. 10*a*-14*b*. The cross sectional shape may also change through different sections over the length of the cannula ribs 22*a*. Additionally, cannula ribs 22*a* may have a continuous length or have non-continuous sections. The cannula ribs 22*a* may provide a user with the ability to manipulate the structure of the cannula body 22 and nasal inserts 30 whereby improving comfort and convenience during use, as well as, improved sealability and air flow.

Figure 8:
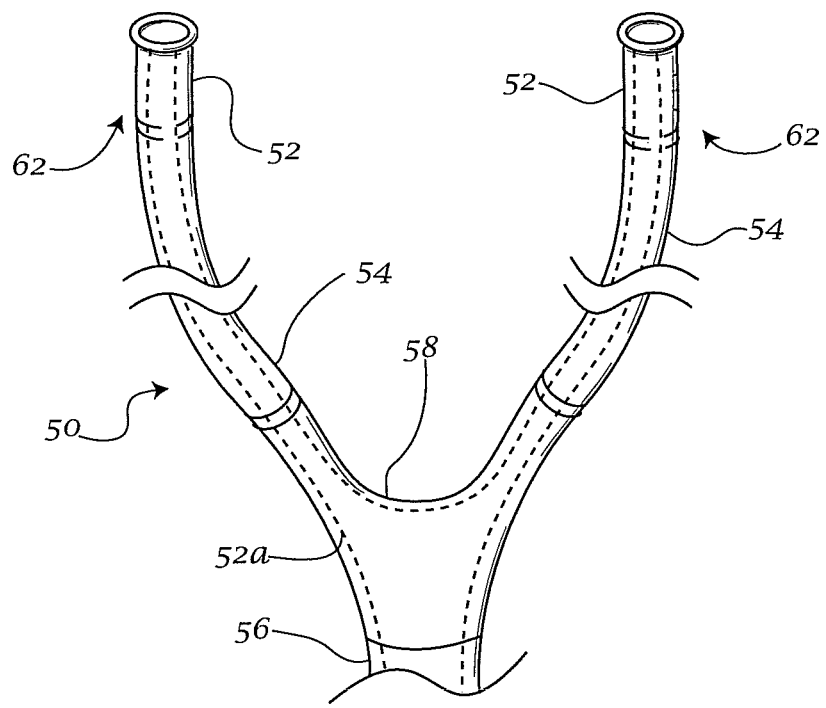
FIG. 8 is an exemplary perspective view of an exemplary embodiment of the ventilation interface with the nasal inserts incorporated into independent supply tubes.
Figure 9C:
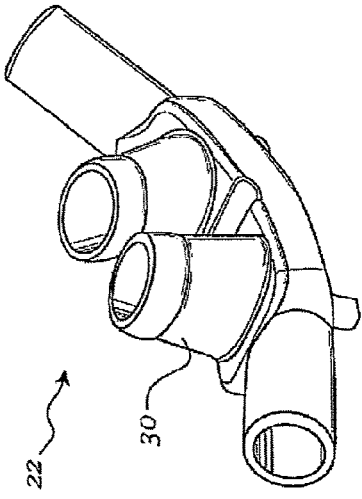
FIG. 9c is an exemplary perspective view of an exemplary ventilation interface embodied in an exemplary nasal cannula body.
Figure 9D:
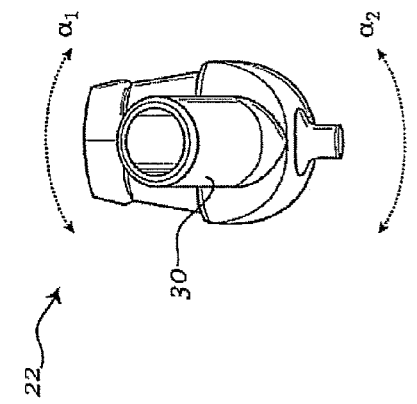
FIG. 9d is an exemplary side view of an exemplary ventilation interface embodied in an exemplary nasal cannula body.
Figure 9A:
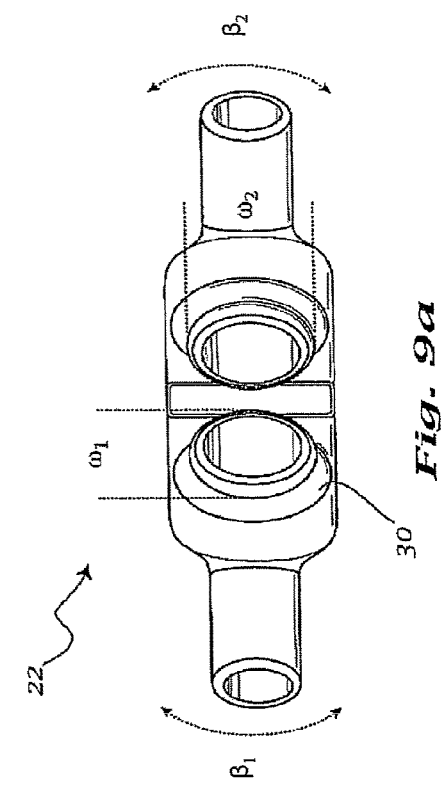
FIG. 9a is an exemplary top view of an exemplary ventilation interface embodied in an exemplary nasal cannula body.
Figure 9B:
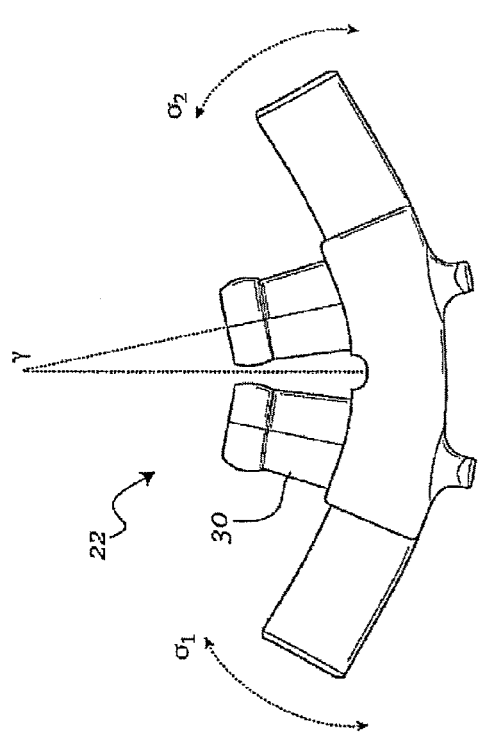
FIG. 9b is an exemplary front view of an exemplary ventilation interface embodied in an exemplary nasal cannula body.
Figure 10A:
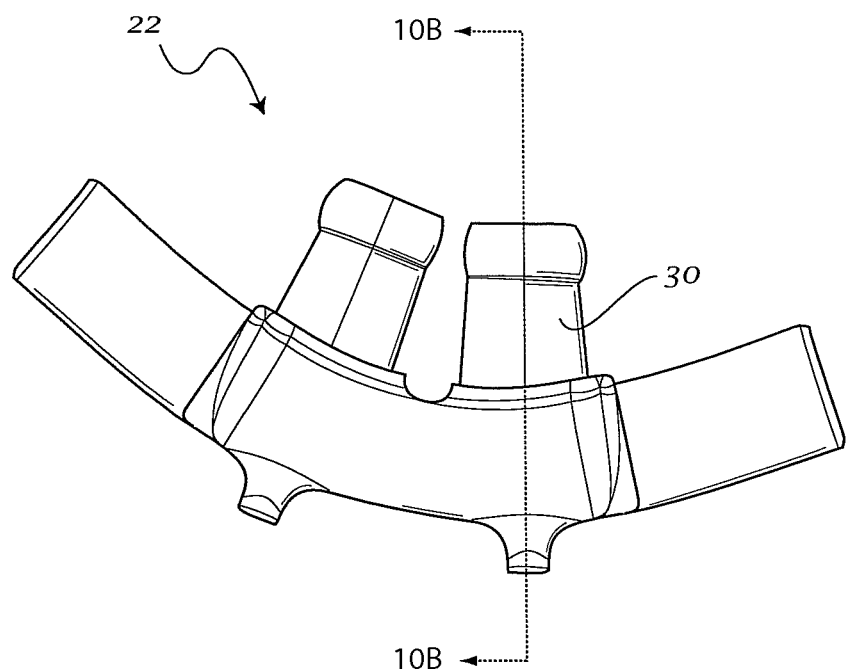
FIG. 10a is an exemplary front view of another exemplary ventilation interface embodied in an exemplary nasal cannula body.
Figure 10B:
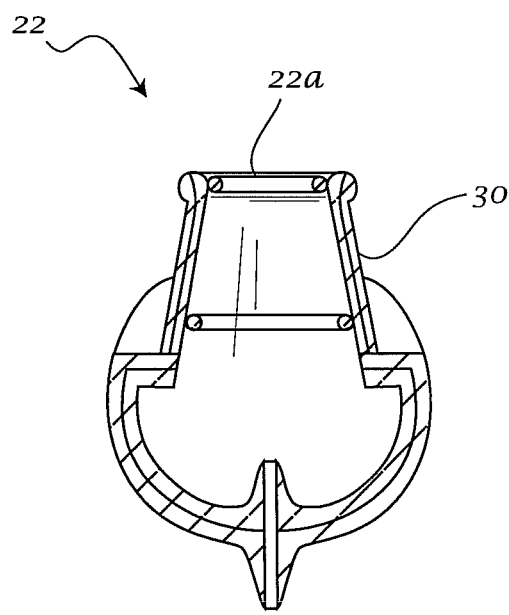
Figure 11A:
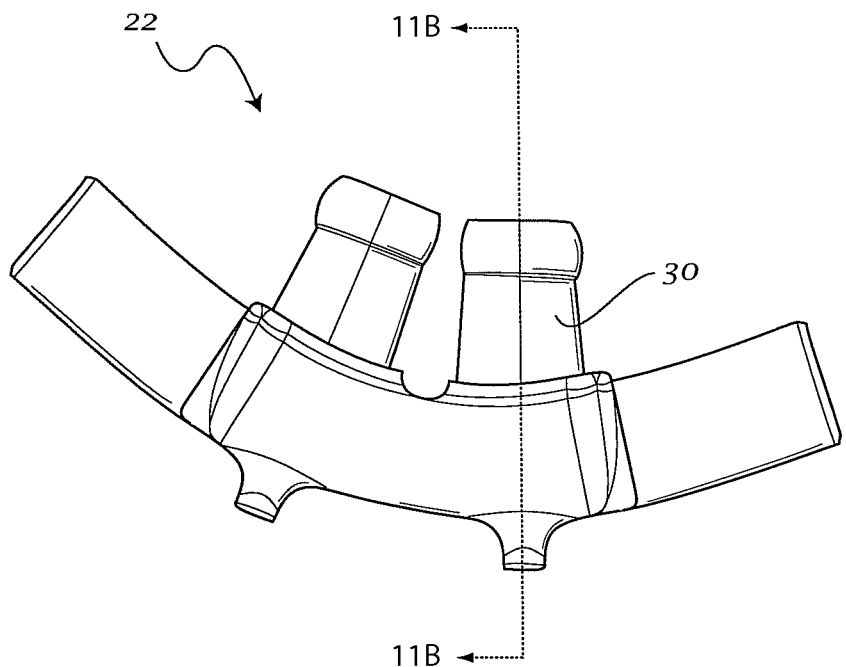
FIG. 11a is an exemplary front view of another exemplary ventilation interface embodied in an exemplary nasal cannula body.
Figure 11B:
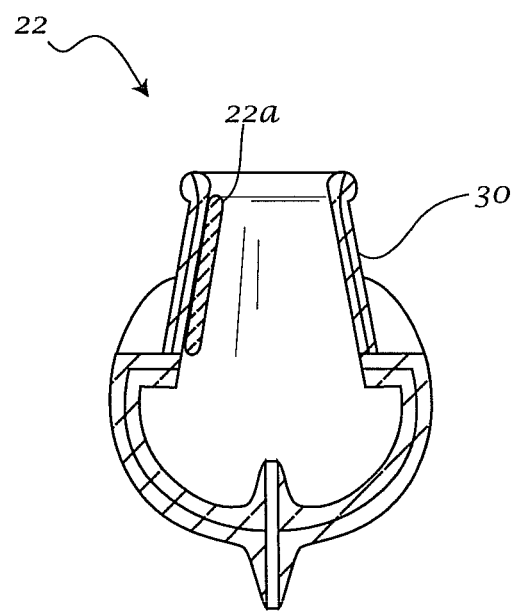
Figure 12A:
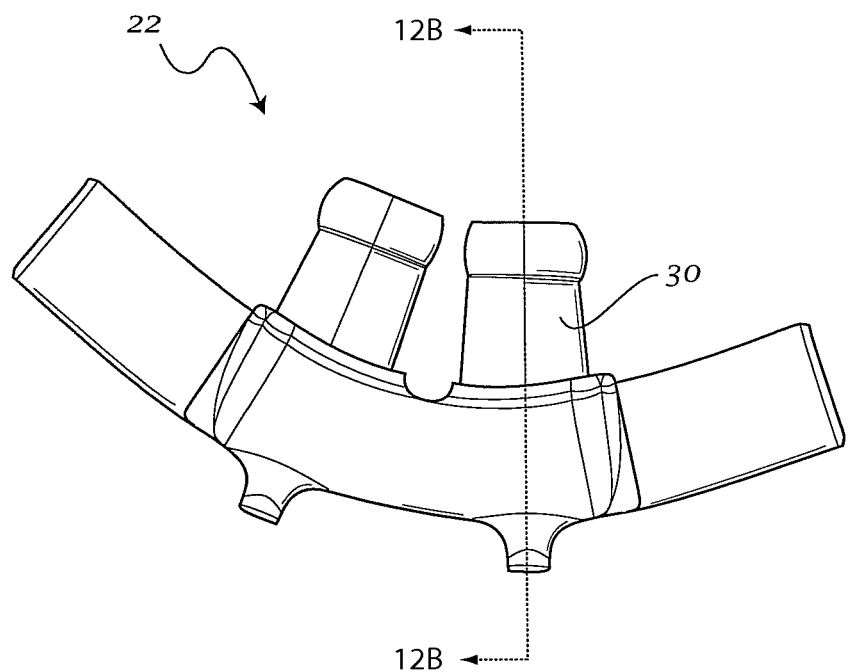
FIG. 12a is an exemplary front view of another exemplary ventilation interface embodied in an exemplary nasal cannula body.
Figure 12B:
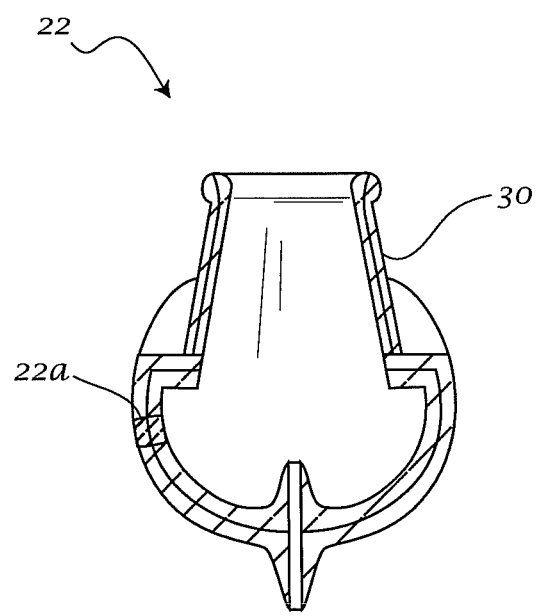
Figure 13A:
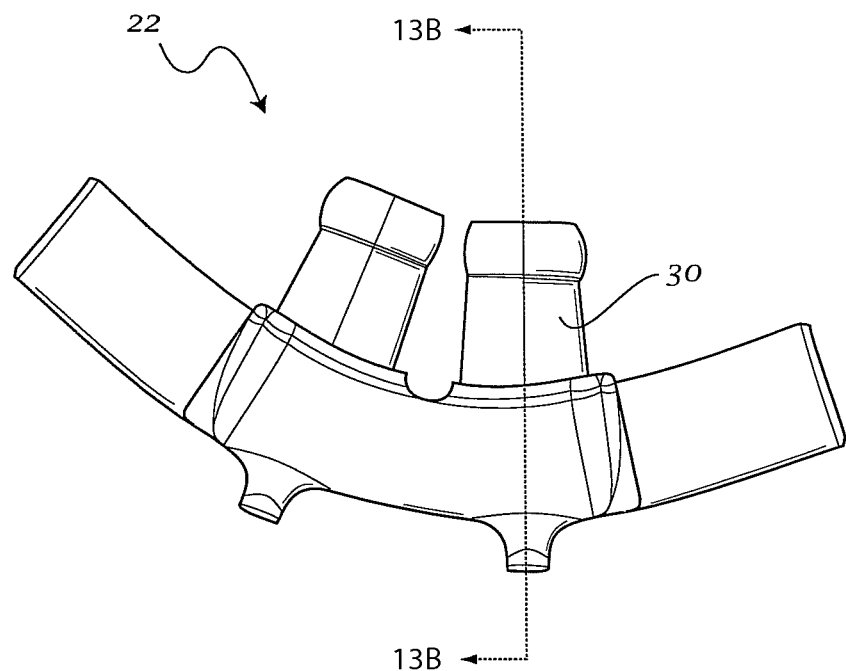
FIG. 13a is an exemplary front view of another exemplary ventilation interface embodied in an exemplary nasal cannula body.
Figure 13B:
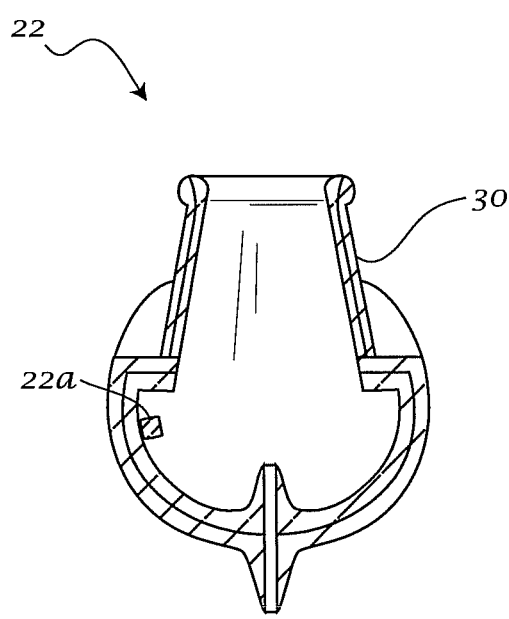
Figure 14A:
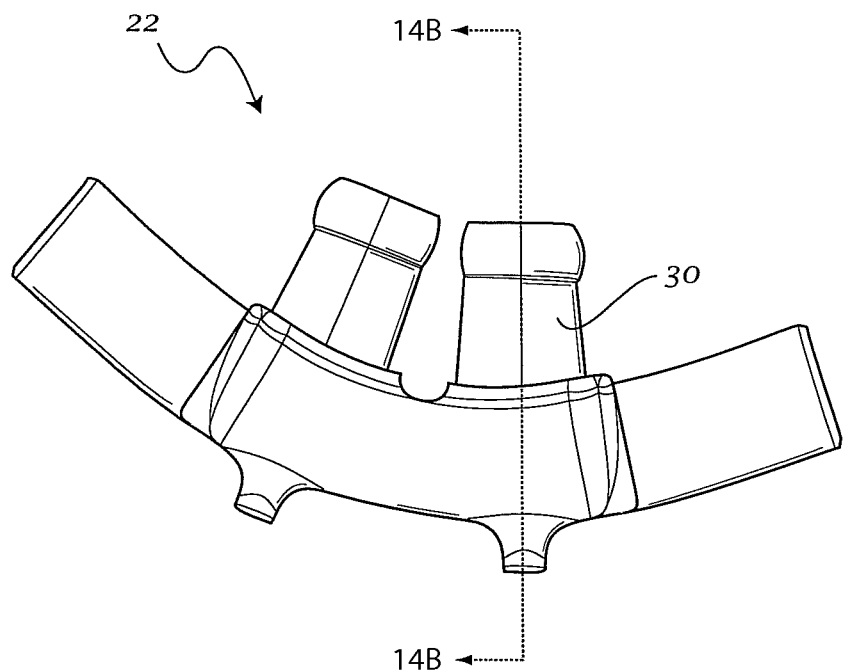
FIG. 14a is an exemplary front view of another exemplary ventilation interface embodied in an exemplary nasal cannula body.
Figure 14B:
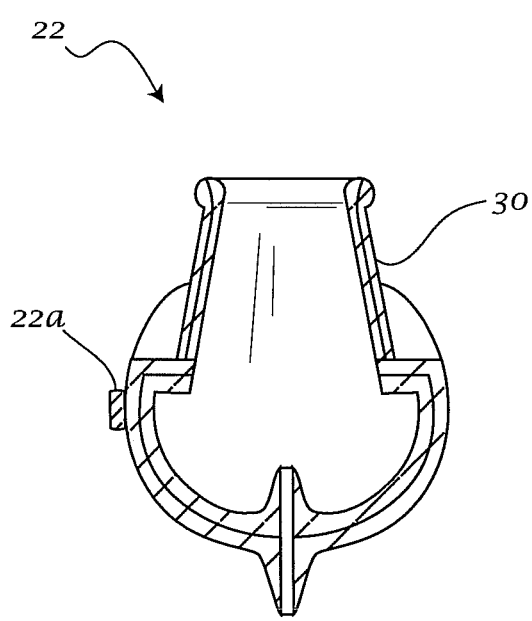
Figure 15A:
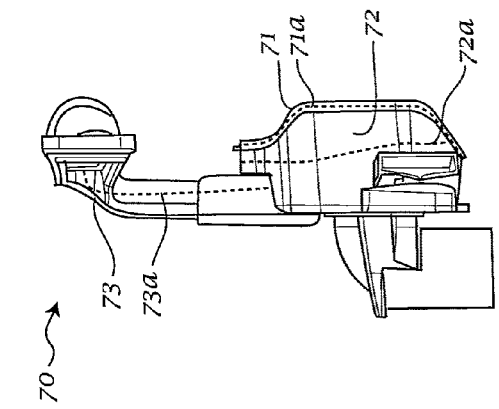
FIG. 15a is an exemplary top view of a further exemplary ventilation interface embodied with a forehead support.
Figure 15B:
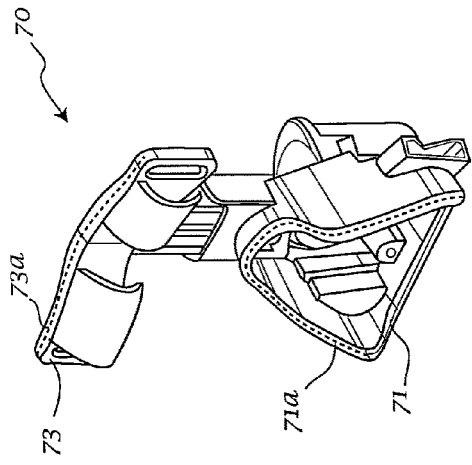
FIG. 15b is an exemplary back view of a further exemplary ventilation interface embodied with a forehead support.
Figure 15C:
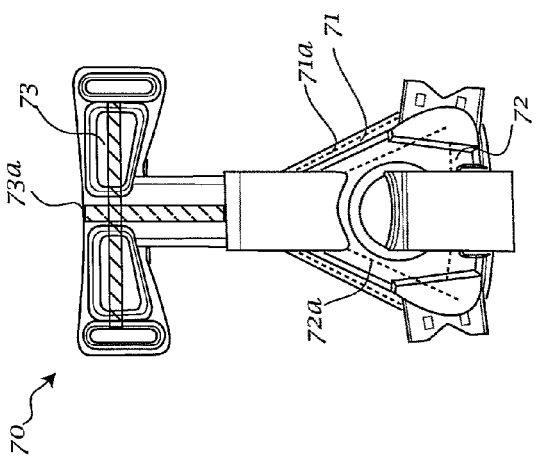
FIG. 15c is an exemplary perspective view of a further exemplary ventilation interface embodied with a forehead support.
Figure 15D:
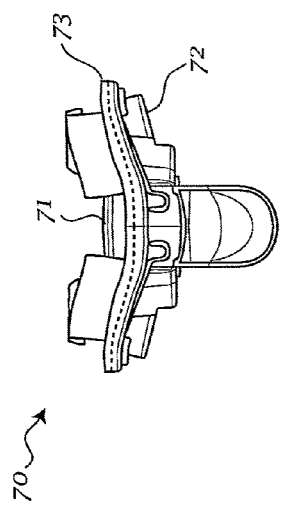
FIG. 15d is an exemplary side view of a further exemplary ventilation interface embodied with a forehead support.
Figure 16D:
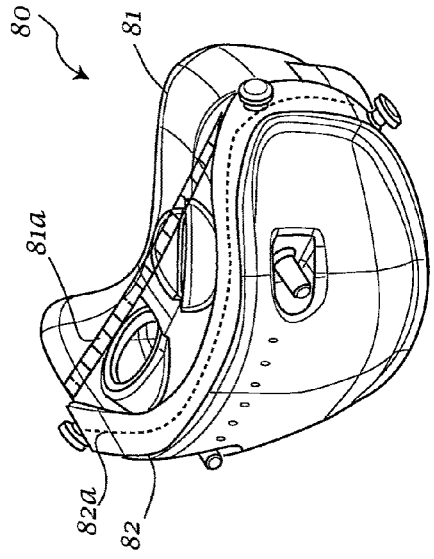
FIG. 16d is an exemplary perspective view of an exemplary ventilation interface mask.
Figure 16E:
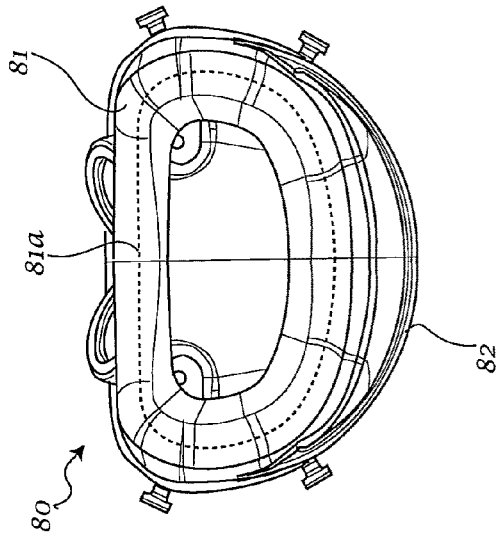
FIG. 16e is an exemplary back view of an exemplary ventilation interface mask.
Figure 16A:
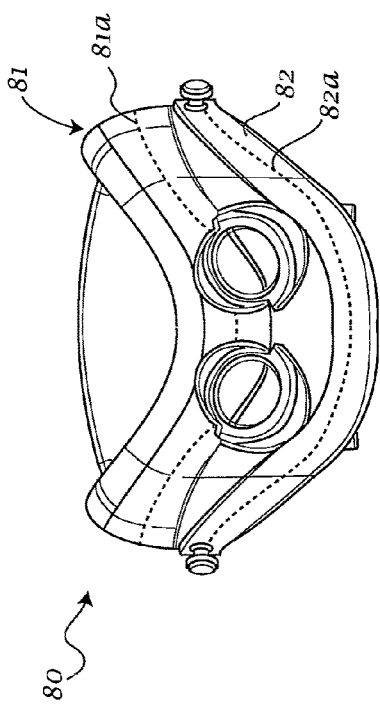
FIG. 16a is an exemplary top view of an exemplary ventilation interface mask.
Figure 16C:
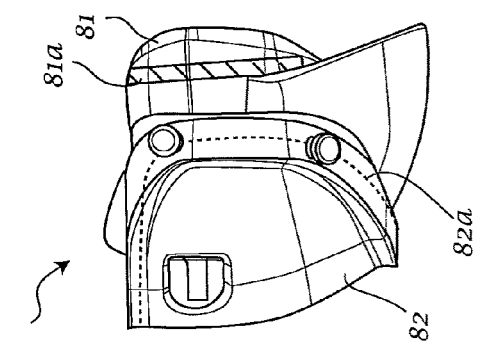
FIG. 16c is an exemplary side view of an exemplary ventilation interface mask.
Figure 16B:
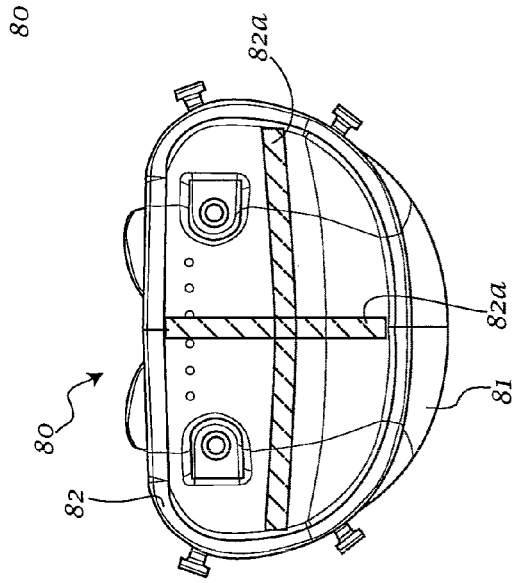
FIG. 16b is an exemplary front view of an exemplary ventilation interface mask.

In a further exemplary embodiment, as seen in figure FIG. 8, the ventilation interface 50 may include nasal inserts 52 which may each be connected to a separate supply tube 54. Supply tubes 54 may be connected to a mechanical ventilator supply hose 56 by a suitable Y-connector 58 or adapter, the cannula body 22 and common air chamber 22*d* may be omitted.

Additionally, for example, nasal inserts 52 may be connected directly to an air or gas supply, supply tubes 54 may be directly connected to an air or gas supply or any other desired structural configuration may be used to supply air or gas to nasal inserts 52 from an air or gas supply. The nasal inserts 52 may have substantially the same construction as nasal inserts 30, or for example, have any other desired construction capable of supplying air or gas to a user.

In another exemplary embodiment, nasal insert 52 may be made from silicone elastomer or any other desired rigid or flexible material. Additionally, supply tubes 54 may be made, for example, from a flexible, lightweight, but relatively inelastic thermoplastic material, similar to heat shrink tubing, so that the supply tubes 54 may be at least partially collapsed in the absence of pressure from the mechanical ventilator.

In another exemplary embodiment, bleeder ports 62 may have a similar construction to the bleeder ports 38, or may not include a bleeder port 62, may include only one bleeder port 62 or include as many bleeder ports as desired. Additionally, for example, bleeder ports 62 may be located on any surface of nasal interface 50 and in any desired configuration with respect to the nasal ports 62.

As seen in FIG. 8 nasal insert 52 may also include nasal insert ribs 52*a* made of memory wire, stiffener or other desired bendable material that may have a greater rigidity than the material composing the main body of the nasal insert 52. Nasal insert 52 may be capable of being contorted into and retaining multiple desired bent shapes. The cross-sectional shape of nasal insert 52 may be altered throughout the entire structure or in only desired or predetermined locations, including, for example, the height, width or general shape in any desired direction. Nasal insert ribs 52*a* may be formed, for example, vertically along the length of nasal insert 52, as seen in FIG. 8, or circumferentially throughout the length of the nasal insert 52 or in any other desired configuration. The number of nasal insert ribs 52*a* used may vary according to preference, ranging from at least one nasal insert rib 52*a*, to as many as desired. The nasal insert ribs 52*a* may also be of any desired length or thickness. Increasing the number and size of nasal insert ribs 52*a* may increase the rigidity of the nasal insert 52 incrementally.

The nasal insert ribs 52*a* may be made of plastic, metal or any other material that may be capable of adding rigidity and shape retention. The nasal insert ribs 52*a* may be manufactured within the walls of the nasal insert 52 or lie on the outer or inner surface of nasal insert 52. The nasal insert ribs 52*a* may be secured to nasal insert 52 by, for example, insert molding, gluing or by any other desired attachment mechanism. Nasal insert ribs 52*a* may also have a variety of different cross sectional shapes, for example, circular, rectangular, square or any other desired shape. The cross-sectional shape may also change through different sections over the length of the nasal insert ribs 52*a*. Additionally, nasal insert ribs 52*a* may have a continuous length or have non-continuous sections. The nasal insert ribs 52*a* may provide a user with the ability to manipulate the structure of the nasal insert 52 whereby improving comfort and convenience during use, as well as, improved seal ability and air flow.

In another embodiment, as seen in FIGS. 15*a*-15*d*, a ventilation interface 70 may include a cushion 71 which may create a seal with the face of a user, a shell 72 which may supply gas to a user, and a forehead support 73 which may aid in the stability of the structure as a whole and add additional comfort to the user.

As seen in FIGS. 15*a*-15*d* the cushion 71, shell 72, and forehead support 73 may also include ribs 71*a*, 72*a* and 73*a* respectively, made of memory wire, stiffener or other desired bendable material that may have a greater rigidity than the material composing the main body of the cushion 71, shell 72, and forehead support 73. Cushion 71, shell 72, and forehead support 73 may be capable of being contorted into and retaining multiple desired bent shapes. The cross-sectional shape of cushion 71 and shell 72 may be altered throughout the entire structure or in only desired or predetermined locations, including, for example, the height, width or general shape in any desired direction. Ribs 71*a*, 72*a* and 73*a* may be formed, for example, vertically along the length of cushion 71, shell 72, and forehead support 73, as seen in FIGS. 15*a*-15*d*, or circumferentially throughout the length of cushion 71, shell 72, and forehead support 73 or in any other desired configuration. The number of ribs 71*a*, 72*a* and 73*a* used may vary according to preference, ranging from at least one rib 71*a*, 72a and 73a, to as many as desired. The ribs 71a, 72a and 73a may also be of any desired length or thickness. Increasing the number and size of ribs 71a, 72a and 73a may increase the rigidity of the cushion 71, shell 72, and forehead support 73 incrementally.

The ribs 71a, 72a and 73a may be made of plastic, metal or any other material that may be capable of adding rigidity and shape retention. The ribs 71a, 72a and 73a may be manufactured within the walls of the cushion 71, shell 72, and forehead support 73 or lie on the outer or inner surface of cushion 71, shell 72, and forehead support 73. The ribs 71a, 72a and 73a may be secured to cushion 71, shell 72, and forehead support 73 by, for example, insert molding, gluing or by any other desired attachment mechanism. Ribs 71a, 72a and 73a may also have a variety of different cross sectional shapes, for example, circular, rectangular, square or any other desired shape. The cross sectional shape may also change through different sections over the length of the ribs 71a, 72a and 73. Additionally, ribs 71a, 72a and 73a may have a continuous length or have non-continuous sections. The ribs 71a, 72a and 73a may provide a user with the ability to manipulate the structure of the cushion 71, shell 72, and forehead support 73 whereby improving comfort and convenience during use, as well as, improved sealability and air flow.

In a further embodiment, as seen in FIGS. 16a-16e, a ventilation interface 80 may include a cushion 81 which may create a seal with the face of a user and a shell 82 which may supply gas to a user.

As seen in FIGS. 16a-16e the cushion 81 and shell 82 may also include ribs 81a and 82a respectively, made of memory wire, stiffener or other desired bendable material that may have a greater rigidity than the material composing the main body of the cushion 81 and shell 82. Cushion 81 and shell 82 may be capable of being contorted into and retaining multiple desired bent shapes. The cross-sectional shape of cushion 81 and shell 82 may be altered throughout the entire structure or in only desired or predetermined locations, including, for example, the height, width or general shape in any desired direction. Ribs 81a and 82a may be formed, for example, vertically along the length of cushion 81 and shell 82, as seen in FIGS. 16a-16e, or circumferentially throughout the length of cushion 81 and shell 82 or in any other desired configuration. The number of ribs 81a and 82a used may vary according to preference, ranging from at least one rib 81a and 82a, to as many as desired. The ribs 81a and 82a may also be of any desired length or thickness. Increasing the number and size of ribs 81a and 82a may increase the rigidity of the cushion 81 and shell 82 incrementally.

The ribs 81a and 82a may be made of plastic, metal or any other material that may be capable of adding rigidity and shape retention. The ribs 81a and 82a may be manufactured within the walls of the cushion 81 and shell 82 or lie on the outer or inner surface of cushion 81 and shell 82. The ribs 81a and 82a may be secured to cushion 81 and shell 82 by, for example, insert molding, gluing or by any other desired attachment mechanism. Ribs 81a and 82a may also have a variety of different cross sectional shapes, for example, circular, rectangular, square or any other desired shape. The cross sectional shape may also change through different sections over the length of the ribs 81a and 82a. Additionally, ribs 81a and 82a may have a continuous length or have non-continuous sections. The ribs 81a and 82a may provide a user with the ability to manipulate the structure of the cushion 81 and shell 82 whereby improving comfort and convenience during use, as well as, improved seal ability and air flow.

Figure 17:
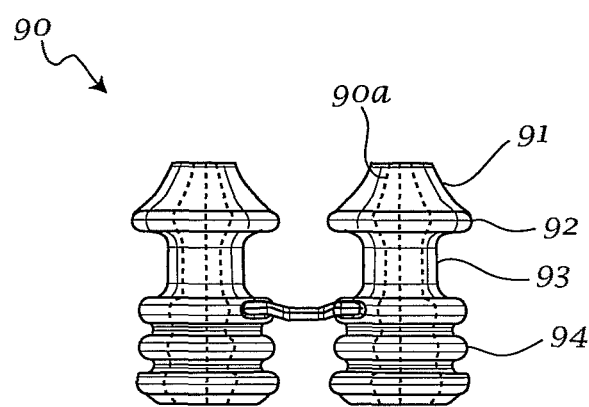
FIG. 17 is an exemplary side view of an exemplary nasal pillow.

FIG. 17 is a generally diagrammatic view of an exemplary embodiment of a nasal pillow 90. Nasal pillow 90 may also include a nasal pillow tip 91, pillow body 92 and pillow neck 93. The nasal pillow tip 91 may be used to rest on the nares of a user. The pillow tip 91 may be made of a thin flexible material as a means of providing a user with a comfortable fit while retaining sealability between the user and the ventilation interface. The pillow body 92 may aid in retaining the structure of the nasal pillow in order to provide adequate gas flow between the user and the ventilation interface. The pillow neck may also aid in providing sufficient gas flow between the ventilation interface and the user by providing a hollow conduit that may be flexible in order to direct each nasal pillow, and specifically the pillow tip 91, to a separate naris of the user.

In this embodiment, each nasal pillow 90 may be connected to a ventilation interface by inserting flange 94 into a receiving opening on a ventilation interface. The flange 94 may provide a seal between the nasal pillow 90 and a ventilation interface, thus preventing leaking or escape of gas exchanged between the user and the ventilation interface. The nasal pillow 90, including the pillow tip 91, pillow body 92, pillow neck 93 and flange 94 may be made from silicone elastomer, and may have the same or different softness, thickness and flexibility throughout the nasal pillow 90.

As seen in FIG. 17 nasal pillow 90 may also include nasal pillow ribs 90a made of memory wire, stiffener or other desired bendable material that may have a greater rigidity than the material composing the tip 91, body 92, neck 93 and flange 94 of the nasal pillow 90. Tip 91, body 92, neck 93 and flange 94 of the nasal pillow 90 may be capable of being contorted into and retaining multiple desired bent shapes. The cross-sectional shape of Tip 91, body 92, neck 93 and flange 94 of the nasal pillow 90 may be altered throughout the entire structure or in only desired or predetermined locations, including, for example, the height, width or general shape in any desired direction. Nasal pillow ribs 90a may be formed, for example, along the length of nasal pillow 90, as seen in FIG. 17, or circumferentially throughout the length of the nasal pillow 90 or in any other desired configuration. The number of nasal pillow ribs 90a used may vary according to preference, ranging from at least one nasal pillow rib 90a, to as many as desired. The nasal pillow ribs 90a may also be of any desired length or thickness. Increasing the number and size of nasal pillow ribs 90a may increase the rigidity of the nasal pillow 90 incrementally.

The nasal pillow ribs 90a may be made of plastic, metal or any other material that may be capable of adding rigidity and shape retention. The nasal pillow ribs 90a may be manufactured within the walls of the nasal pillow 90 or lie on the outer or inner surface of nasal pillow 90. The nasal pillow ribs 90a may be secured to nasal pillow 90 by, for example, insert molding, gluing or by any other desired attachment mechanism. Nasal pillow ribs 90a may also have a variety of different cross sectional shapes, for example, circular, rectangular, square or any other desired shape. The cross-sectional shape may also change through different sections over the length of the nasal pillow ribs 90a. Additionally, nasal pillow ribs 90a may have a continuous length or have non-continuous sections. The nasal pillow ribs 90a may provide a user with the ability to manipulate the structure of the nasal pillow 90 whereby improving comfort and convenience during use, as well as, improved sealability and air flow.

It is to be understood that the present invention is not limited to the embodiments described above, but encompasses any and all embodiments within the scope of the following claims.

What is claimed is:

1. A respiratory interface, comprising:
a nasal interface, wherein the nasal interface comprises:
   a hollow body;
   a nasal insert;
   a flange about an exterior surface of the nasal insert, the flange adapted to lodge against the interior of the naris of a user; and
   a shapeable rib coupled with a distal portion of the nasal insert adapted to be inserted into the nostril of the user,
wherein the shapeable rib has a length and a rib cross-section normal to said length, wherein the rib cross-section is parallel to a cross-sectional shape of the nasal insert, and wherein the said cross-sectional shape of the nasal insert is adapted to be altered by the user to at least two different fixed shapes when the user reshapes the shapeable rib.

2. The respiratory interface of claim 1, wherein the nasal interface comprises a plurality of shapeable ribs.

3. The respiratory interface of claim 1, wherein the shapeable rib is circumferentially oriented about the nasal insert.

4. The respiratory interface of claim 1, wherein the shapeable rib is longitudinally oriented about the nasal insert.

5. The respiratory interface of claim 1, wherein the shapeable rib is directly attached to an inner surface of the nasal insert.

6. The respiratory interface of claim 1, wherein the shapeable rib is directly attached to an outer surface of the nasal insert.

7. The respiratory interface of claim 1, wherein the nasal insert is composed of a material and the shapeable rib is directly attached within the material of the nasal insert.

8. The respiratory interface of claim 1, further comprising a second nasal insert.

9. The respiratory interface of claim 1, wherein the shapeable rib is further coupled with the flange.

10. A respiratory interface configured to be in flow communication with at least one of a user's nostrils, the respiratory interface comprising:
at least one nasal insert with a distal portion and a proximal portion,
wherein the distal portion is adapted to be inserted into the nostril of the user, wherein the nasal insert includes:
   a hollow body;
   a flange about the nasal insert; and
   a shapeable rib coupled with the distal portion of the nasal insert and configured to maintain at least two different shapes, wherein the shapeable rib has a length and a rib cross-section normal to said length, wherein the rib cross-section is parallel to a cross-sectional shape of the at least one nasal insert, and
wherein the shapeable rib is adapted to be reshaped by the user in order to alter the cross-sectional shape of the distal portion of the at least one nasal insert.

11. The respiratory interface of claim 10, wherein the length of the shapeable rib is not parallel to an axis of the nasal insert.

12. The respiratory interface of claim 10, wherein the shapeable rib is circumferentially oriented about the nasal insert.

13. The respiratory interface of claim 10, wherein the shapeable rib is non-spiral in shape.

14. The respiratory interface of claim 10, wherein the shapeable rib does not extend the entire length of the nasal insert.

15. The respiratory interface of claim 10, wherein the shapeable rib does not extend to a distal tip of the nasal insert.

16. A respiratory interface, comprising:
a nasal interface, wherein the nasal interface comprises:
   a hollow body with a side surface and a bottom surface that merge to form an air chamber;
   a nasal insert coupled with the hollow body; and
   a shapeable rib coupled with a distal portion of the nasal insert adapted to be inserted into the nostril of the user, and configured to maintain at least two different shapes,
wherein the shapeable rib has a length and a rib cross-section normal to said length, wherein the rib cross-section is parallel to a cross-sectional shape of the nasal interface, and wherein the said cross-sectional shape of the nasal interface is adapted to be altered by the user when the user reshapes the shapeable rib.

17. A respiratory interface configured to be in flow communication with at least one of a user's nostrils, the respiratory interface comprising:
at least one nasal insert, wherein the nasal insert includes:
   a hollow body;
   a flange about the nasal insert; and
   at least two shapeable ribs configured to maintain at least two different shapes and coupled with a distal portion of the at least one nasal insert adapted to be inserted into the nostril of a user, wherein the at least two shapeable ribs have a length and a rib cross-section normal to said length wherein the rib cross-section is parallel to a cross-sectional shape of the at least one nasal insert, wherein the at least two shapeable ribs are adapted to be reshaped by the user in order to alter the cross-sectional shape of the at least one nasal insert.

* * * * *